United States Patent [19]

Hembre et al.

[11] 4,388,217

[45] Jun. 14, 1983

[54] PROCESS FOR THE RECOVERY OF CATALYST VALUES

[75] Inventors: Robert T. Hembre; Steven L. Cook, both of Kingsport, Tenn.

[73] Assignee: Eastman Kodak Company, Rochester, N.Y.

[21] Appl. No.: 304,773

[22] Filed: Sep. 23, 1981

Related U.S. Application Data

[63] Continuation-in-part of Ser. No. 209,798, Nov. 24, 1980, abandoned.

[51] Int. Cl.$^3$ .................... B01J 31/40; B01J 23/96; C07C 51/10; C01G 55/00
[52] U.S. Cl. ............................ 252/413; 252/414; 252/415; 260/549; 423/22; 562/607
[58] Field of Search ............. 252/413, 414, 415, 420; 260/549, 546; 562/607, 608; 423/22, 179.5

[56] References Cited

U.S. PATENT DOCUMENTS

| | | | |
|---|---|---|---|
| 3,420,873 | 1/1969 | Olivier | 252/415 |
| 3,857,895 | 12/1974 | Booth | 568/455 |
| 3,887,489 | 6/1975 | Fannin et al. | 252/414 |
| 3,927,078 | 12/1975 | Lapporte et al. | 260/549 |
| 4,046,807 | 9/1977 | Kuckertz | 260/549 |
| 4,188,363 | 2/1980 | Fell et al. | 423/22 |
| 4,234,719 | 11/1980 | Wan | 260/549 |
| 4,340,569 | 7/1982 | Davidson et al. | 423/22 |
| 4,340,570 | 7/1982 | Davidson | 423/22 |
| 4,341,741 | 7/1982 | Davidson et al. | 423/22 |
| 4,364,907 | 12/1982 | Barnes | 423/22 |

*Primary Examiner*—P. E. Konopka
*Attorney, Agent, or Firm*—J. Frederick Thomsen; Daniel B. Reece, III

[57] ABSTRACT

Disclosed is a process for the recovery of catalyst values from a catalyst-tar solution derived from a production system in which acetic anhydride is prepared by carbonylating methyl acetate in the presence of rhodium, lithium and methyl iodide. The catalyst values are recovered by submitting the catalyst-tar solution to an extraction using methyl iodide and aqueous hydrogen iodide. The presence of hydrogen iodide in the aqueous phase stabilizes the rhodium in a water-soluble form and prevents rhodium losses due to the rhodium plating out on the process equipment.

4 Claims, No Drawings

PROCESS FOR THE RECOVERY OF CATALYST VALUES

This is a continuation-in-part application of Ser. No. 209,798 filed Nov. 24, 1980, now abandoned.

This invention relates to a novel process for recovering rhodium catalysts values and, more particularly, to a method for recovering rhodium values from "tars" formed during the preparation of acetic anhydride by the rhodium-catalyzed carbonylation of methyl acetate.

The use of catalyst systems comprising rhodium and an iodine compound in the preparation of acetic anhydride by the carbonylation of methyl acetate has been reported in the patent literature. See, for example, Belgian Pat. No. 819,455, British Published Patent Application No. 2,013,184, Japanese Published Patent Application Nos. 75-47921 and 75-47922 and U.S. Pat. Nos. 3,927,078 and 4,046,807. Those publications also disclose that the reaction rate can be increased if the catalyst system contains a promoter such as certain amines, phosphines and inorganic materials such as lithium compounds. The use of amines and phosphines, particularly under conditions giving high space-time yields, causes formation of tars which cannot be handled in a continuous process. The use of lithium compounds, such as lithium iodide or lithium acetate, does not entirely avoid the formation of tar but the tar that is formed is not unmanageable.

Tar formation, which is essentially unavoidable in the carbonylation of methyl acetate, increases as reaction conditions, such as temperature and pressure, are increased to obtain a desirably high space-time yield such as 400 g./l./hr. or greater. It is known (U.S. Pat. No. 4,046,807) that the inclusion of hydrogen in the gas feed to the carbonylation reactor in a system employing triphenylphosphine can suppress tar formation. If not removed from the reaction system, tar will increase to the point where catalyst activity is greatly diminished which can eventually result in the termination of the carbonylation reaction.

Because of the cost of rhodium, high-efficiency catalyst recycling in the rhodium-catalyzed carbonylation of methyl acetate is of extreme importance for the successful operation of an acetic anhydride process. A survey of the literature on recovery/recycling procedures for rhodium species from reaction mixtures reveals a variety of methods relying on selective reduction and deposition of rhodium metal from these mixtures (Published German Patent Application No. 2,262,852; Japanese Published Patent Application No. 77-045,425) or simply oxidation/incineration of the tar materials to volatile species and collection of the nonvolatile $Rh/Rh_2O_3$ remains (U.S. Pat. Nos. 3,920,449 and 4,135,911). In the methyl acetate carbonylation process, the catalytically active form of rhodium has been identified as the anion $[Rh(CO)_2I_2]^\ominus$. This knowledge coupled with the expectation that tar formed in the process will be largely hydrocarbon in nature suggested that aqueous extraction might be a viable technique for the separation of rhodium values from anhydride tar by-products.

While water extracts much of the rhodium present in the tar, the resulting solution is not stable at elevated temperatures resulting in much of the rhodium being lost from the system through deposits on the process equipment. This instability of the water-soluble rhodium species is a serious shortcoming of the aqueous extraction technique since the amount of water in the rhodium-containing solution recycled to the carbonylation reactor must be minimized to avoid undue decomposition of the acetic anhydride being produced.

We have discovered that the inclusion of HI in the water used to extract rhodium values from the above-described tars stabilizers the soluble rhodium species, thereby increasing the overall efficiency of the extraction and recycling of the rhodium employed in the carbonylation process. The aqueous HI also recovers lithium and iodine values, primarily as lithium iodide. It is also essential that a water-immiscible, organic solvent for the tar be used in combination with the aqueous HI solution. Methyl iodide is a particularly suitable organic solvent since it is used in the carbonylation system.

Typically, the tar is removed continuously or intermittently from the carbonylation system in the form of a solution in a mixture of the compounds present in the system. The catalyst-tar solution may be removed either from the reactor or, in the case of a system employing a liquid product take-off from the reactor, from some point in the normal catalyst recycle stream. The solution can be submitted to the aqueous/organic solvent extraction or can be concentrated by stripping off some of the liquids present. In production facilities in which the rhodium is recycled to the reactor, the tar-containing recycle stream normally will have been concentrated to some extent in the product recovery section of the facilities.

The process in which the tar is formed comprises the preparation of acetic anhydride by the liquid phase carbonylation of methyl acetate in the presence of rhodium and an iodine compound at elevated pressure and temperature wherein a feed mixture containing methyl acetate is continuously fed to a carbonylation reactor and a reaction mixture containing acetic anhydride is continuously removed. Optionally, a catalyst such as a lithium compound can be used and up to about 7 volume percent of the carbon monoxide gas may consist of hydrogen. In the practice of the process, the feed to the reactor is such as to maintain within the reaction mixture (1) about 250 to 1300 ppm, preferably about 500 to 1000 ppm, Rh, (2) about 175 to 5000 ppm, preferably about 1500 to 3700 ppm, lithium and (3) about 7 to 35 weight percent methyl iodide. The remainder of the reactor contents consists mostly of methyl acetate reactant and acetic anhydride product with minor amounts of by-products such as ethylidene diacetate and acetone. The reactor feed optionally may contain a solvent such as acetic acid, e.g. in an amount that will maintain about 5 to 40 weight percent in the reaction mixture. In a liquid take-off system, the catalyst components, e.g. the rhodium, lithium and iodine as methyl iodide, are recovered from the reactor effluent and are recycled. When necessary, fresh rhodium, as rhodium chloride, rhodium acetate or other rhodium containing compound, and lithium, as lithium hydroxide, lithium iodide, lithium acetate or other lithium-containing compound are added to the catalyst recycle. The fresh rhodium and lithium can be conveniently added as a solution in acetic acid. When the iodine needs to be supplemented it may be added to the system as iodine ($I_2$), as methyl iodide or, at least in part, as lithium iodide. In a vapor take-off system, all or essentially all of the rhodium and lithium catalyst components remain in the reactor and thus, the risk of their depletion from the process is reduced considerably. The tar material formed in the process has very reproducible, but poorly resolved spectral features. These features appear in tars formed in both liquid and vapor take-off as well as from runs with both high and low tar formation rates.

From the combined information of IR, H NMR, C NMR, and elemental analysis, certain aspects of the "structure" may be proposed; however, the poor resolution in the H and C NMR spectra thwart hopes for absolute identification and are suggestive of a highly amorphous material. The C NMR shows two major broad band absorptions of approximately equal intensity, one in the alkyl region (13–45 $\delta$) and the other in the aromatic region (120–140 $\delta$). For the same material, the H NMR shows almost no aromatic protons relative to the alkyl bands at 0.9–1.7 $\delta$ and 1.6–3.0 $\delta$. In combination, these two spectra, therefore, suggest a polyalkylated aromatic material substituted to the exclusion of aromatic protons. Additionally, the C shows some very minor absorptions assignable to carbonyl moieties, a feature strongly suggested by the IR band at 1700 cm$^{-1}$. The IR also suggests carbon-oxygen (1180 cm$^{-1}$) and oxygen-hydrogen (36–3300 cm$^{-1}$) bonds. The elemental analysis substantiates the expectations of per aromatic unsaturation showing 0.60 unsaturations per carbon and an empirical formula of $C_{36}H_{41}O_4I_{0.15}$. Despite the ambiguities of actual tar structure, in a practical sense it is readily soluble in organic solvents and has proven amenable to liquid/liquid extraction.

The amounts of aqueous HI and methyl iodide that can be used to satisfactorily removed the rhodium values from the catalyst-tar solution will vary substantially depending on a number of factors such as the concentration of the tar in the liquids removed from the production system, the amount of rhodium present in the tar, the rhodium extraction efficiency that is desired, and the type of apparatus that is used. The anionic rhodium species that is present in the catalyst-tar solution is soluble in the quantity of methyl iodide that is normally used in the process of this invention. In the presence of water, however, the rhodium is preferentially dissolved in the aqueous phase. Thus, the use of larger amounts of water will result in more of the total rhodium that will be present in the aqueous phase. The use of large amounts of water will also permit optimum phase separation by avoiding emulsion formation. However, the use of relatively large amounts of water will require a concentration step in the process.

As stated above, the aqueous phase containing most of the rhodium removed from the acetic anhydride normally should be minimized before the rhodium is returned to the process. The purpose for doing so is to minimize the amount of anhydride decomposition that is caused by water which could significantly affect the overall anhydride yield of the process. The use of very large amounts of water therefore can cause an undue amount of energy to be used in the concentration step and thereby increase operating costs disproportionately to the value of the rhodium recovered.

It has been discovered that in certain types of operation the amount of acetic acid, derived from the acetic anhydride and acid phase of the extraction solvent system has, as does the amount of water used, a significant effect on the rhodium distribution coefficient (RDC) defined as [Rh] Methyl Iodide/[Rh] Water. To obtain a RDC of at least about 0.5, preferably at least about 0.25, the concentration of acetic acid in the aqueous phase should not be more than about 8 weight percent and preferably not more than about 4 weight percent. To achieve such an acetic acid concentration while avoiding the use of economically undesirable amounts of water, the catalyst-tar solution is concentrated to a weight of at least 50 percent, preferably, to a weight of at least 30% of the catalyst-tar solution removed from the acetic anhydride process. Concentrating the catalyst-tar solution results in a distillate containing methyl iodide, methyl acetate, acetic anhydride and acetic acid which can be combined with the concentrated aqueous phase and recycled to the carbonylation reactor.

The amount of hydrogen iodide required will vary depending on such factors as the amount of lithium acetate present and the temperatures to which the aqueous phase is heated. Normally, sufficient hydrogen iodide is used so that the pH of the aqueous phase is about 1 or less, preferably in the range of about 0.6 to 0.8. The concentration of the HI solution can be varied from concentrated (47%) aqueous HI down to about 6 weight percent. The amount of methyl iodide employed should be at least about 2 parts per weight per part of concentrated catalyst-tar mixture. Methyl iodide ratios of about 3 to 5 (same basis) have been found to give good results.

In the practice of our process, a portion of the liquid contents containing tar and rhodium, lithium and iodine values is removed intermittently or continuously from the carbonylation system and fed to a hold tank. The tar solution then can be fed periodically to a still-decanter fitted with means for agitation. The composition of the tar solution will vary depending, for example, upon the point from which it is taken from the carbonylation system. Initially, low boiling components such as methyl iodide and methyl acetate along with some acetic acid and acetic anhydride are removed to give a concentrated solution of the tar and rhodium catalyst in acetic anhydride and acetic acid. Methyl iodide and the aqueous hydrogen iodide are added to the concentrated solution with agitation. In batch operations best results are obtained if the methyl iodide is added first to the concentrated solution which has been cooled to just below the boiling point of methyl iodide. After partitioning, agitation is stopped, the aqueous and organic layers are allowed to separate and the methyl iodide phase containing the tar is removed from the bottom of the still-decanter. The remaining aqueous solution of hydrogen iodide and rhodium, lithium and iodine values in water and acetic acid is vacuum distilled to remove most of the water, e.g. 90%. The remaining catalyst solution can then be combined with the liquids initially removed and recycled to the carbonylation reactor.

The methyl iodide and tar may be separated by distillation and the viscous tar-methyl iodide residue can be treated further to remove any iodine and rhodium values present. The water and methyl iodide recovered in the process can be recycled for use in the next extraction.

The process may be modified to provide for continuous operation by feeding catalyst-tar solution, aqueous hydrogen iodide and methyl iodide simultaneously to a mix tank and feeding the mixture to about the midpoint of an extraction column. An aqueous stream containing most of the catalyst values is removed from the top of the column and the methyl iodide containing the tar is removed from the bottom. Normally, additional aqueous hydrogen iodide and methyl iodide are added to the lower and upper portions, respectively, of the extraction column.

The practice of the process is further illustrated by the following examples. The tar employed in the examples resulted from a carbonylation system comprising a 3.5 liter reactor consisting of five feet five inches of two-inch Sch. 40 pipe. A gas mixture of carbon monoxide and 5 volume percent hydrogen is fed through a gas sparger at the bottom of the reactor. Through a reactor feed line, located above the sparger, is fed a mixture containing methyl acetate, acetic acid, acetic anhydride, methyl iodide, lithium and rhodium at an average rate of about 12,600 grams/hour. The composition of the feed stream normally is 18–20% methyl iodide, 55–40% methyl acetate, 15–20% acetic acid, 15–20% acetic anhydride, about 750 ppm rhodium and about 3500 ppm lithium. Using this system acetic anhydride is produced at about 750 psig and 190° C. at a space time yield of about 600 grams/liter-hour. The reactor contents overflow from the top of the reactor to a reactor separator pot where some of the unreacted carbon monoxide and other gases are separated from the liquid and purged from the system. The liquid from the reactor separator pot passes through a valve which reduces the pressure from about 750 psig to 10–20 psig. The liquid passes through a flash evaporator, wherein about 80–90% of the material is vaporized and enters an evaporator separator pot (about 1 psig) wherein the vapor and liquid are separated. The liquid, which consists mainly of acetic acid and acetic anhydride in which the rhodium and lithium catalyst components are dissolved along with minor amounts of methyl iodide and methyl acetate, is recycled to the reactor. The vapors from the evaporator separator pot are fed to a column in which the temperature is maintained at about 140° C. at the base and about 100° C. at the top. Crude acetic anhydride suitable for further refining is removed from the lower portion of the column. The low boilers (methyl acetate, methyl iodide and some acetic acid) are taken overhead and fed to a low boiler blend tank to which makeup methyl acetate is also fed. The contents of the blend tank are continuously fed to the reactor feed line. The tar solutions used in the examples are obtained from the above-described catalyst recycle stream (catalyst heel).

EXAMPLE 1

A sample of catalyst heel was taken after 112 hours of acetic anhydride production as described above during which the weight ratio of tar formation to anhydride production was 0.00022. A 152.2 g. portion of the catalyst heel material was concentrated to about 40 g. on a rotary evaporator (95° C., 30 minutes, 5–10 torr), dissolved in methyl iodide/13% (aqueous) hydrogen iodide, partitioned, and separated to give 80.0 g. aqueous phase and 70.9 g. organic phase. Two additional extractions of the organic phase with 13% (aqueous) HI followed. The rhodium analytical results and balance calculations for each extraction are listed below. All analytical samples were dissolved in 10% (v/v) HCl/DMF and compared with previously prepared standards in the [Rh] range of 0–20 ppm where adsorption is linearly dependent on concentration. The listed uncertainty (±) for each analysis is the product of the dilution necessary to reach the desired [Rh] and a measurement accuracy of ±0.1 ppm.

| Extraction | Phase | Wt. (g.) | [Rh] (ppm) | Wt. Rh (mg) | % Total Rh |
|---|---|---|---|---|---|
| 1st | Organic | 70.9 | 42.5 ± 1.7 | 3.9 | 1.5 |
|  | Aqueous | 79.5 | 2473.6 ± 4.8 | 196.6 | 98.5 |
| 2nd | Organic | 65.3 | 21.6 ± 1.0 | 1.4 | 0.7 |
|  | Aqueous | 50.2 | 22.9 ± 1.1 | 1.2 | 0.6 |
| 3rd | Organic | 59.9 | 14.0 ± 0.9 | 0.8 | 0.4 |
|  | Aqueous | 36.0 | 6.8 ± 1.3 | 0.2 | 0.1 |

Rhodium Balance: $Rh_{initial}$ = 199.6 mg
Rh (aq) final = 198.0 mg (99.2%)
Rh (org) final = 0.8 mg (0.4%)
Rh (samples) = 0.2 mg (0.1%)

$$\% \text{ Accountability} = \left( \frac{\text{total Rh final}}{\text{total Rh}_{initial}} \right) 100$$

% accountability = 99.7

$$\% \text{ Efficiency} = \left( \frac{Rh(aq.) \text{ final}}{\text{total Rh}_{initial}} \right) 100$$

% efficiency = 99.2

EXAMPLE 2

1.95 g. of dried tar, [Rh]=7938 ppm (C/Rh=739 by elemental analysis), initial 15.4 mg., resulting from a procedure similar to Example 1 was dissolved in 31.7 g. MeOAc, 13.7 g. acetic acid, 12.7 g. methyl iodide, and 3.25 g. lithium iodide trihydrate. Following concentration on a rotary evaporator (90° C., 45 minutes, 5–10 torr), dissolution in methyl iodide/conc. (aq) HI, partitioning, and separation the methyl iodide was stripped from the organic phase leaving 1.90 g. dry granular solid with [Rh]=1139 ppm, (C/Rh=4645 by elemental analysis), 2.2 mg. The aqueous phase, 102.8 g, contained $[Rh]_{(aq)}$=127.0 ppm, 13.1 mg.

| Rhodium Balance: | |
|---|---|
| Rh initial = 15.4 mg | Rh(aq), final = 13.1 mg (85.0%) |
|  | Rh(tar), final = 2.2 mg (14.3%) |
|  | Accountability = 93.3% |
|  | Efficiency = 85% |

This example shows that previously extracted tar from which all of the volatile components have been removed may be submitted to a second extraction to recover additional rhodium.

EXAMPLE 3

19.3 g. anhydride tar and 199.9 g. conc. (aq) HI were placed in a 250 ml. round bottom flask with a magnetic stir bar. After stirring 15 minutes, a sample of aqueous solution was extracted and analyzed for $[Rh]_{initial}$=151 ppm. The solution was then heated to reflux for three hours and a second sample extracted and analyzed for $[Rh]_{final}$=156 ppm.

EXAMPLE 4

23.5 g. anhydride tar and 100 ml. H₂O were placed in a 250 ml. round bottom flask with a magnetic stir bar. After stirring 15 minutes a sample of aqueous solution was extracted and analyzed for $[Rh]_{initial}$=304.7 ppm. The solution was then heated to reflux for three hours and a second sample extracted and analyzed for $[Rh]_{final}$=1.5 ppm.

EXAMPLE 5

5.0 g. anhydride tar dissolved in 45.6 methyl iodide and 50 ml. conc. (aq) HI. After partitioning and separation a sample of the aqueous phase was placed in a vial, then 10 ml. was diluted to 75 ml. Atomic adsorption analysis of undiluted and the dilute samples were taken. The solutions were allowed to sit for 80 hours at room temperature, then analyzed for rhodium as shown below:

[Rh]$_{conc.}$, i=309 ppm; [Rh]$_{conc.}$, f=229 ppm;
[Rh]$_{dil.}$, i=41 ppm; [Rh]$_{dil.}$, f=44 ppm.

A sample prepared just as above with H$_2$O instead of conc. (aq) HI was also prepared and sat with the above samples.

[Rh]$_{(aq)}$, i=169 ppm; [Rh]$_{(aq)}$, f=53 ppm.

Examples 3, 4 and 5 demonstrate the stabilizing effect which hydrogen iodide has on the water soluble rhodium species.

EXAMPLES 6-11

Samples of tar-containing catalyst recycle solution were taken from the above-described methyl acetate carbonylation system after 120, 274, 340, 438, 508 and 796 hours of operation. Each of the samples along with some acetic acid were charged to a 3-liter, 3-neck flask fitted with a stirrer, means for charging materials to the flask, and means for distilling off, condensing and collecting liquid materials from the flask. The flask also has a bottom drain for removing liquid which may be fed to a second 3-neck flask (1 liter) which also has a stirrer, is fitted with a condenser so that vaporized material can be removed, condensed and collected and has a bottom drain tube.

The catalyst recycle-acetic acid solution is concentrated by distilling under vacuum for about one hour at 400 torr initial pessure and a final pressure and base temperature of 150 torr and 95° C. To the cooled residue is added with stirring methyl iodide and then dilute aqueous HI over a total time of about 20 minutes. External cooling is employed as necessary to maintain the temperature between about 25° and 50° C. The mixture is stirred for an additional five minutes and then the aqueous and organic layers are permitted to separate over a period of 10 minutes. The drain stopcock is opened and the methyl iodide layer containing the tar is transferred to the 1-liter flask. Most of the methyl iodide is stripped off at atmospheric pressure and a temperature of about 41°-50° C. While the tar residue is hot, it is drained into another container. Since the tar residue contains some methyl iodide and acetic acid, a small sample is further stripped at 6 torr, 100° C. for 30 minutes to give a more accurate tar value.

The rhodium-containing aqueous HI remaining in the 3-liter flask was stripped at 140-160 torr until the base temperature reached 95°-97° C. The concentrated solution then was drained from the flask, combined with the distillate first collected in the process and added to the carbonylation reactor feed line.

The amounts of materials used and recovered, analytical data pertaining thereto and the rhodium extraction efficiency for each of Examples 6-11 are shown in Table I. Part I of the Table gives the amounts of catalyst recycle solution (CRS) and acetic acid (HOAc) initially charged, the amount and weight percent composition of the distillate collected (MeI=methyl iodide, MeOAc=methyl acetate, Ac$_2$O=acetic anhydride, EDA=ethylidene diacetate) and the amount of rhodium in the residue. Part II gives the amounts of methyl iodide and concentrated (45%) aqueous HI and water used in the extraction. Step III shows the amount of methyl iodide recovered from the 1-liter flask, the amount of tar, both with and without volatiles, the amount of rhodium in the tar and the extraction efficiency (EE). Step 4 of the Table gives the amount of the distillate, and the amount of acetic acid contained therein, resulting from the concentration (water removal) of the aqueous phase of the aqueous/organic solvent extraction step.

TABLE I

| | Examples | | | | | |
|---|---|---|---|---|---|---|
| | 6 | 7 | 8 | 9 | 10 | 11 |
| Step I | | | | | | |
| Charge, g. | | | | | | |
| CRS | 580.0 | 510.2 | 562.4 | 610.0 | 620.8 | 510.3 |
| HOAc | 131.2 | 83.0 | 77.4 | 66.7 | 103.1 | 15.7 |
| Distillate, g. | 458.7 | 400.0 | 390.0 | 396.1 | 439.4 | 302.1 |
| MeI | 2.0 | 1.1 | 1.7 | 1.0 | 0.9 | 1.0 |
| MeOAc | 15.2 | 9.6 | 22.2 | 14.1 | 12.4 | 7.8 |
| Acetone | None | 0.3 | 1.9 | 0.2 | 2.5 | Trace |
| HOAc | 56.4 | 58.1 | 49.8 | 50.2 | 48.7 | 32.2 |
| Ac$_2$O | 25.9 | 30.1 | 24.0 | 34.1 | 34.9 | 51.7 |
| EDA | 0.3 | 0.8 | 0.3 | 0.4 | 0.4 | 0.9 |
| Rh, g. | 2.553 | 1.022 | 1.608 | 2.295 | 1.973 | 1.204 |
| Step II | | | | | | |
| MeI | 938.7 | 892.9 | 901.0 | 904.1 | 900.7 | 888.2 |
| Conc. HI | 151.1 | 150.1 | 150.0 | 150.1 | 149.9 | 152.4 |
| H$_2$O | 743.3 | 758.1 | 750.0 | 744.0 | 740.7 | 750.0 |
| Step III | | | | | | |
| MeI | 878.8 | 842.0 | 805.2 | 815.8 | 818.4 | 799.5 |
| Tar, g. | 87.7 | 45.3 | 39.7 | 47.5 | 63.0 | 63.2 |
| Tar less Volatiles | — | 33 | 28 | 29 | 44 | 47 |
| Rh, mg | 248 | 140 | 236 | 358 | 75 | 66 |
| EE, % | 90.3 | 86.3 | 85.3 | 84.4 | 96.2 | 94.5 |
| Step IV | | | | | | |
| Distillate, g. | 779.2 | 835.7 | 845.1 | 807.7 | 783.4 | — |
| HOAc, g. | 96.6 | 154.8 | 234.6 | 295.2 | 97.8 | — |

EXAMPLE 12

This example describes a continuous process for the recovery of catalyst values from a catalyst-tar solution obtained from a methyl acetate carbonylation process as described hereinabove. The description of each process stream refers to the hourly flow rate by weight of each component thereof. This modification of the process allows the water requirement to be reduced to such an extent that the water removal step can be eliminated.

A catalyst-tar solution consisting of 38 parts MeI, 8 parts acetone, 79 parts MeOAc, 333 parts HOAc, 938 parts Ac$_2$O, 47 parts EDA, 428 parts LiI, 62 parts LiOAc (lithium acetate), 7.2 parts rhodium and 144 parts tar is fed to a flash evaporator. The vapor stream containing all of the MeI and acetone, 70 parts MeOAc, 283 parts HOAc, 619 parts Ac$_2$O and 8 parts EDA is condensed and fed to a volatiles receiver. The liquid phase from the evaporator is fed to an agitated tank (stripped tar receiver) to which is also fed a stream of MeI (752 parts) and a stream, taken from the midpoint of the continuous extractor, consisting of 850 parts MeI, 43 parts MeOAc, 164 parts water, 481 parts HOAc, 39 parts EDA, 554 parts LiI, 161 parts HI (100% hydrogen iodide), 7.2 parts rhodium and 144 parts tar. The stream consisting of MeI is derived from a reflux condenser to which is fed MeI vapors from the stripped tar receiver and the continuous extractor. Two reactions take place in the receiver. Hydrogen iodide reacts with the lithium acetate in the stripped tar feed to form lithium iodide and acetic acid. Acetic acid is also formed when water reacts with residual acetic anhydride in the stripped tar mixture. The presence of the HI in the receiver also stabilizes the rhodium and thus prevents the rhodium from precipitating and plating out on the walls of the receiver and equipment downstream. The catalyst values and the tar are initially partitioned between the aqueous and organic phases in the agitated stripped tar receiver.

A stream from the receiver, after passing through a filter to remove any insoluble tar, is fed to the midpoint of a continuous, counter-current fractional extraction column where further partitioning and separation of the catalyst values and tar occurs. The extractor feed stream consists of 850 parts MeI, 52 parts MeOAc, 962 parts HOAc, 108 parts water, 78 parts EDa, 1108 parts LiI, 41 parts HI, 14.4 parts rhodium and 288 parts tar. The continuous extractor employed is a Karr reciprocating plate extraction column. For a detailed description of this type of extractor see Karr, A. E., AIChE Journal, 5, 446 (Dec. 59); Karr, A. E., and Lo, T. C., Proceedings of the International Solvent Extraction Conference, "Society of Chemical Industry", (London), Vol. 1, 299 (1971); Karr, A. E., and Lo, T. C., Chemical Engineering Progress, 72, 68 (Nov. 76); Karr, A. E. and Lo, T. C., Proceedings of the International Solvent Extraction Conference, Toronto, 1977; and Bulletin KC-11 of CHEM-PRO Equipment Corporation. A stream of 850 parts MeI, 21 parts MeOAc and 3 parts water consisting of recycled MeI obtained from the methyl iodide evaporator (referred to hereinafter) and, if necessary, fresh methyl iodide is fed to the upper portion, preferably near the top, of the extractor. An aqueous HI solution typically containing 155 parts water and 161 parts HI is fed to the lower portion, preferably near the bottom, of the extractor. The HI concentration of the aqueous HI solution is controlled to maintain the apparent pH of the aqueous phase at about 1 or less, preferably in the range of about 0.5 to 0.8, to prevent the rhodium from depositing on the walls and/or plates of the extractor. The amount of HI required to maintain the desired pH can vary depending on the amount of lithium acetate contained in the stripped tar solution.

An overflow stream consisting primarily of the aqueous phase containing acetic acid and most of the catalyst values and an underflow stream consisting primarily of the organic methyl iodide phase containing the tar are continuously removed from the extractor. The overflow stream containing 2 parts MeI, 10 parts MeOAc, 99 parts water, 465 parts HOAc, 551 parts LiI, 41 parts HI and 6.1 parts rhodium is fed to an agitated catalyst recycle tank where it is combined with the condensed volatiles of the volatiles receiver (referred to hereinabove). The combined streams then may be fed to the carbonylation reactor.

The extractor underflow stream containing 848 parts MeI, 20 parts MeOAC, 3 parts water, 20 parts HOAc, 39 parts EDA, 3 parts LiI, 1.1 parts rhodium and 144 parts tar is fed to a methyl iodide stripper wherein about 99% of the methyl iodide is evaporated away from the tar. The vapor stream containing 842 parts MeI, 20 parts MeOAc and 3 parts water is condensed, fed to a methyl iodide hold tank and recycled to the upper portion of the extractor column. The non-volatilized components consisting of 6 parts MeI, 20 parts HOAc, 39 parts EDA, 6 parts LiI, 1.1 parts rhodium and 144 parts tar can be submitted to further treatment such as another extraction or incineration to recover remaining catalyst values.

The invention has been described in detail with particular reference to preferred embodiments thereof, but it will be understood that variations and modifications can be effected within the spirit and scope of the invention.

We claim:

1. Process for the recovery of catalyst values from a catalyst-tar solution derived from a production system in which acetic anhydride is prepared by carbonylating methyl acetate in the presence of rhodium, lithium and methyl iodide wherein the catalyst-tar solution is submitted to an extraction using methyl iodide and aqueous hydrogen iodide and recovering catalyst values in the aqueous phase.

2. Process according to claim 1 wherein the pH of the aqueous hydrogen iodide phase is about 1 or less.

3. Process for the removal of tar from a production system in which acetic anhydride is prepared by carbonylating methyl acetate in the presence of rhodium, lithium and methyl iodide which comprises the steps of:
   (1) forming a concentrated catalyst-tar solution containing catalyst values dissolved therein and derived from the production system;
   (2) submitting the catalyst-tar solution to an extraction using methyl iodide and aqueous hydrogen iodide to obtain a methyl iodide phase containing tar and an aqueous phase containing catalyst values; and
   (3) feeding the aqueous phase to the production system, whereby rhodium is maintained in its catalytically-active, water-soluble form to avoid loss of rhodium during the tar removal process.

4. Process according to claim 3 wherein the pH of the aqueous hydrogen iodide is about 1 or less.

* * * * *